United States Patent [19]

Laico et al.

[11] Patent Number: 4,804,372

[45] Date of Patent: Feb. 14, 1989

[54] PROTECTIVE SHEATH FOR HYPODERMIC NEEDLE

[76] Inventors: Joseph P. Laico, 62 S. Mtn. Rd., New City, N.Y. 10956; Joseph L. Molino, 2 Aura Dr., Valley Cottage, N.Y. 10989

[21] Appl. No.: 93,750

[22] Filed: Sep. 8, 1987

[51] Int. Cl.⁴ ............................................. A61M 5/32
[52] U.S. Cl. ...................................... 604/198; 604/263
[58] Field of Search ................ 604/198, 192, 187, 263

[56] References Cited

U.S. PATENT DOCUMENTS

| | | |
|---|---|---|
| 2,571,653 | 10/1951 | Bastien . |
| 2,845,065 | 7/1958 | Gabriel . |
| 4,139,009 | 2/1979 | Alvarez . |
| 4,356,822 | 11/1982 | Winstead-Hall . |
| 4,373,526 | 2/1983 | Kling . |
| 4,425,120 | 1/1984 | Sampson et al. . |
| 4,573,976 | 3/1986 | Sampson et al. . |
| 4,631,057 | 12/1986 | Mitchell . |
| 4,643,200 | 2/1987 | Jennings, Jr. . |
| 4,664,654 | 5/1987 | Strauss ................................ 604/198 |
| 4,772,272 | 9/1988 | McFarland ......................... 604/198 |

Primary Examiner—John D. Yasko
Attorney, Agent, or Firm—Chilton, Alix & Van Kirk

[57] ABSTRACT

A protective needle sheath is operatively extendable for protecting the sharpened needle point of a hypodermic syringe. The sheath comprises a pair of telescopic enclosure shields mounted to the needle base. Detent locking members lock the shields in a non-retractable extended protective position. The sheath is maintained in protective position about the needle in the event that the needle is detached from the syringe body.

20 Claims, 3 Drawing Sheets

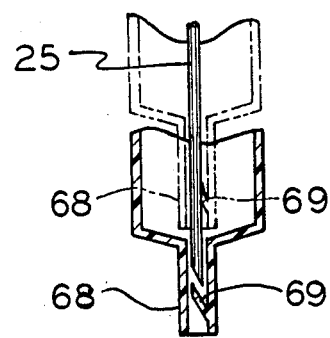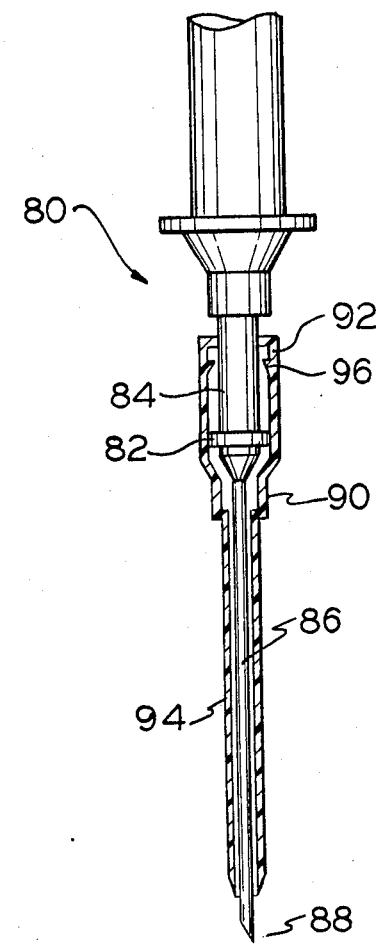

PROTECTIVE SHEATH FOR HYPODERMIC NEEDLE

BACKGROUND OF THE INVENTION

This invention relates generally to hypodermic needles which are adapted to inject substances into humans and animals and/or to withdraw specimens therefrom. More particularly, the present invention relates generally to protective devices which are employed for shielding the needle of a hypodermic syringe or other injecting or withdrawing device.

The vast majority of hypodermic needles are disposable-type needles which are discarded after use. The shielding of the sharp end of the hypodermic needle is of critical concern to health practitioners both in relation to needle disposal and to handling the needle. Accidental exposure to the sharp end of the needle can have very serious and even fatal health consequences. For example, the needle may be contaminated with diseases such as hepatitis and A.I.D.S. It is well documented that accidental puncture with a contaminated needle could result in infection with such diseases. Because the hypodermic needle is frequently used during times of emergency or high stress, it is highly desirable that the needle be immediately shielded after usage in a reliable and efficient manner which provides a high degree of protection from accidental puncture.

A variety of different types of devices for shielding a hypodermic needle against inadvertent needle exposure have been advanced. A number of shield devices involve a sleeve-like member for enclosing the sharp end of the needle. Mitchell U.S. Pat. No. 4,631,057 discloses a shielded needle wherein a needle guard is mounted on the body of the hypodermic syringe. The needle guard moves from a retracted position in which the guard does not shield the needle to an extended position in which the guard shields the needle. The needle guard can be locked in the extended position by interlocking members carried by the needle guard and a collar which is mounted on the body of the syringe.

Sampson et al U.S. Pat. No. 4,573,976 discloses a shielded needle wherein a needle guard is mounted on the body of the syringe. In an extended position, the needle guard obstructs access to the point of the needle. In a retracted position, the guard does not obstruct access to the point of the needle. The guard may be releasably retained in the retracted position. Interlocking members on the syringe body and the guard are responsive to generally axial movement of the guard to the extended position to prevent reverse movement of the guard toward the retracted position.

SUMMARY OF THE INVENTION

Briefly stated, the invention in a preferred form is a new and improved protective needle sheath for a hypodermic needle. The needle may be employed in a hypodermic syringe of a type having a main body which forms a container for the substance to be injected, or withdrawn, a hypodermic needle including a needle mounting base and means for affixing the base to the syringe body. The protective sheath also has applicability in connection with needles employed in numerous injection or withdrawing devices such as intravenous tubing and catheters. A protective shield assembly is slidably mounted to the base of the needle for shielding the needle point in an extended axial position. The protective shield assembly is axially spaced from the needle point in the retracted position to permit exposure of the needle.

The shield assembly comprises a pair of telescoping concentric, generally cylindrical shields which are generally coaxial with the needle. A mounting flange projects transversely from the needle base. The inner shield defines a generally cylindrical surface which axially slides across the peripheral edge of the mounting flange. The sleeve has an end wall portion and an interior locking means which is engageable with the flange to lock the inner shield in a fixed axial position wherein the shield encloses a portion of the needle. At the opposite distal end of the inner shield a radially projecting lock ring is formed. The outer shield defines a generally cylindrical surface which axially resistably slides across the peripheral edge of the extension. At a proximal end of the second shield an interior locking means is engageable with the lock ring to lock the outer shield in a fixed axial position with the inner shield wherein the outer shield encloses the needle point and a portion of the needle.

Each of the shield locking means preferably comprises a plurality of angularly spaced, radially inwardly projecting detents. The detents are configured to lock the shields in a non-retractable axially extended position wherein the shields are highly resistant to movement to the initial retracted position. The outer shield has a reduced tubular guide portion which slidably engages the needle between the retracted and extended positions and encloses the needle point in the extended position.

An object of the invention is to provide a new and improved protective needle sheath for a hypodermic needle.

Another object of the invention is to provide a new and improved protective needle sheath of efficient construction which may be easily extended to a non-retractable protective position for obstructing access to the sharpened end of the hypodermic needle.

Another object of the invention is to provide a new and improved protective needle sheath of inexpensive construction which is relatively easy to manufacture and assemble on a hypodermic needle.

A further object of the invention is to provide a new and improved protective needle sheath which is mountable to the needle portion of a hypodermic syringe or other injection or withdrawal device so as to remain attached to the needle in the protective position in the event that the needle is dismounted from the main syringe or device body.

A yet further object of the invention is to provide a new and improved protective needle sheath which is operable to impart a high degree of protection from accidental contact with the syringe needle after usage.

Other objects and advantages of he invention will become apparent from the drawing and the specification.

BRIEF DESCRIPTION OF THE DRAWINGS

FIG. 5 is an enlarged fragmentary sectional view, partly in phantom, of a needle and modified embodiment of a protective sheath of the present invention; and FIG. 6 is a side view of an intravenous catheter and a sectional view of another protective sheath embodiment of the present invention illustrated in an extended mode wherein the catheter needle is protected.

DETAILED DESCRIPTION OF THE INVENTION

Figure 1:
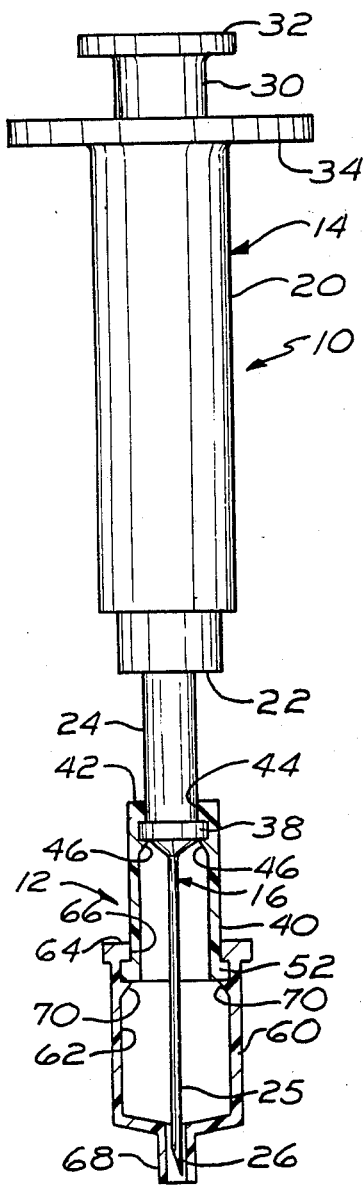
FIG. 1 is a side elevational view of a hypodermic syringe and a sectional view of a protective sheath of the present invention illustrated in an extended mode wherein the syringe needle is protected.

With reference to the drawings wherein like numerals represent like parts throughout the figures, a hypodermic syringe designated generally by the numeral 10, except for the modifications described herein, has a generally conventional form and function. The hypodermic syringe 10 mounts a protective sheath assembly 12 in accordance with the present invention. The syringe 10 generally comprises a main syringe body 14 and a hypodermic needle 16. The sheath assembly 12 is adapted for protecting the distal sharpened end of the syringe hypodermic needle 16 after usage of the syringe. The protective sheath assembly 12 has applicability for syringes employed for injecting substances and/or drawing specimens. Accordingly, the syringe 10 may assume numerous embodiments and configurations in accordance with the invention.

The main syringe body 14 includes a generally cylindrical barrel or vial 20 which receives the substance injected by the syringe and/or the specimen withdrawn by the syringe. The vial 20 constitutes the principal body portion of the syringe. A needle socket 22 or anchoring head is formed at one end of the syringe body 40 for receiving the hypodermic needle 16.

Figure 4:
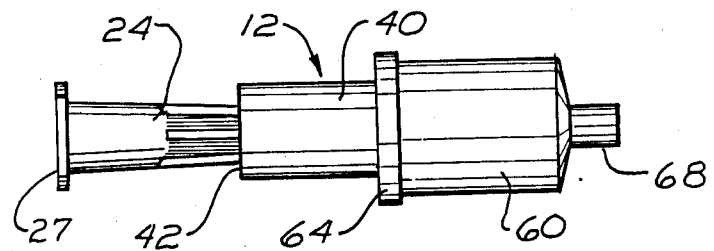
FIG. 4 is a side view of the protective sheath of FIG. 1 and the hypodermic needle portion of an alternate syringe embodiment illustrating the relationship between the needle and the sheath when the needle is disconnected from the main syringe body.

The hypodermic needle 16 includes an integral upper mounting base 24 which tapers into a cannula 25 having distal sharpened point 26. The mounting base 24 is generally of an elongated cylindrical form which fixedly mounts or is anchored by the socket 22 of the syringe body 14. The hypodermic needle 16 may be mounted to the syringe body by a molding process wherein the socket or anchoring head is formed. The hypodermic needle 16 may be either permanently affixed to the main syringe body or detachable therefrom as illustrated in FIG. 4. An axial fluid passage 28 extends from the vial through the needle and opens at the sharpened point in a conventional manner.

A wide variety of means for affixing or mounting the base 24 of the hypodermic needle to the mounting body of the syringe may be provided. For example, in FIG. 4 a Luer-type connector 27 connects the mounting base with the main syringe body. The mounting base 29 also has a generally tapered shape which convergingly tapers from the connecting end portion toward the needle.

A plunger 30 is mounted for axial displacement within the vial 20 for forcing the substance from the vial through the axial passage of the hypodermic needle and/or drawing a specimen or substance through the needle into the vial. The plunger 30 includes an upper plunger handle 32. A transversely extending upper wing 34 of the syringe body cooperates with the plunger handle to permit facile manipulation of the syringe. It should be understood that the invention has applicability with numerous types and forms of hypodermic syringes and the illustrated syringe embodiment is described merely for purposes of illustrating the invention.

The needle base 24 includes an elongated cylindrical portion which extends from the connector end of the syringe body. An annular retainer flange 38, which may be a washer or similar component or an integrally molded structure, radially extends from a lower portion of the mounting base 24 in coaxial relationship with the cannula and the main body 14.

The needle sheath assembly 12 comprises an inner sleeve-like shield 40 and a outer sleeve-like shield 60 which are disposed in telescoping relationship with respect to the hypodermic needle 16. Shields 40 and 60 are preferably formed from a rugged resilient plastic material. The shields are manually displaceable in telescoping fashion from the retracted position of FIG. 2 to the non-retractable extended position of FIG. 1 to provide a protective sheath for the hypodermic needle. Although two telescoping shields are illustrated, more than two telescoping shields may be employed.

Inner shield 40 is a sleeve-like member of generally cylindrical structure having a generally uniform inside diameter along the axial length of the shield. The uniform diameter is commensurate with the outside diameter of the retainer flange 38 so that the shield is closely resistably engageable against the peripheral edge of the flange to maintain the shield in the retracted axial position of FIG. 2. The inner shield 40 includes an upper end retainer wall 42 which forms a central aperture 44. The edges of the aperture 44 closely engage the outside surface of the needle mounting base 24 to permit resistant sliding movement therealong.

Integral equiangularly spaced radially protruding detents 46 extend inwardly from the shield. The detents 46 include a generally longitudinally extending tapered surface which leads to a transversely projecting engagement shoulder 48. When the inner shield 40 is axially displaced to the extended position as described hereinafter, the shield flexes or deforms to allow the tapered surfaces of the detents to ride over the peripheral edge of the flange 38 until the engagement shoulders 48 engage against the underside of the retainer flange 38. The retaining flange is essentially captured between the engagement shoulders and the shield end 42 in a non-retractable snap-fit type locking relationship which is highly resistant to disengagement. The engagement shoulders 48 are thus axially spaced from the shield end retainer wall 42 a distance which is commensurate with the axial thickness of the retainer flange 38. The outer distal end of shield 40 includes an integral circumferential lock ring 52 which radially projects from the shield in symmetric coaxial relationship therewith.

Outer shield 60 comprises a generally cylindrical surface 62 having a uniform inside diameter which is commensurate with the outside diameter of the lock ring 52. The lock ring 52 of the inner shield is slidably frictionally engaged by the inner surface of the cylindrical surface 62 for maintaining the shield 60 in the retracted position of FIG. 2 and yieldingly resisting movement to the extended position. An upper end wall 64 of shield 60 defines a central aperture 66 having edge defining surfaces which closely engage the outer cylindrical surface of the inner shield 40. The axial distal portion of shield 60 convergingly tapers to a reduced tubular extension 68. Tubular extension 68 is an axially extending structure of relatively rigid form which has an inside diameter slightly greater than that of the cannula 25. The tubular extension 68 essentially functions as a guide sleeve which moves along the cannula 25 when the protective shield is moved to the extended position. The extension cooperates with the cannula to enhance the mounting integrity between the protective sheath and the syringe. In the extended position, the tubular extension 68 surrounds the sharpened needle point and obstructs contact with the sharpened needle point to thereby constitute the principal protective structure for the needle sheath.

With reference to FIG. 5, a secondary shield in the form of a flap 69 extends integrally inwardly from extension 68 into the sleeve opening. As the tubular extension 68 is moved from the retracted position toward the extended positions, the flap 69 resiliently engages and slides along the cannula 25, as illustrated by dashed lines. In the extended position, the flap 69 is axially positioned beyond the sharpened needle point and projects into the sleeve opening so as to form a secondary shield which obstructs access to the sharpened needle point 26 from the axial end of the tubular extension. The secondary shield provided by the flap 69 further ensures against accidental puncture with the sharpened needle.

Equiangularly spaced detents 70 which are similar in form and function to detents 46 project inwardly from shield 60 at an upper axial position thereof. Detents 70 include transverse engagement shoulders 72 which engage the underside of the lock ring 52 of the inner shield. Shield 60 also flexes or deforms so that the tapered surfaces of the detents 70 ride over the peripheral edge of lock ring 52. The detents 70 cooperate with the end wall 64 of the shield 60 which engages the upper surface of the lock ring 52 to capture the lock ring 52 in a snap-fit locking engagement. The locking engagement is highly resistant to retractive disengagement to thereby maintain the outer shield 60 in the locked extended position of FIG. 1.

Figure 2:
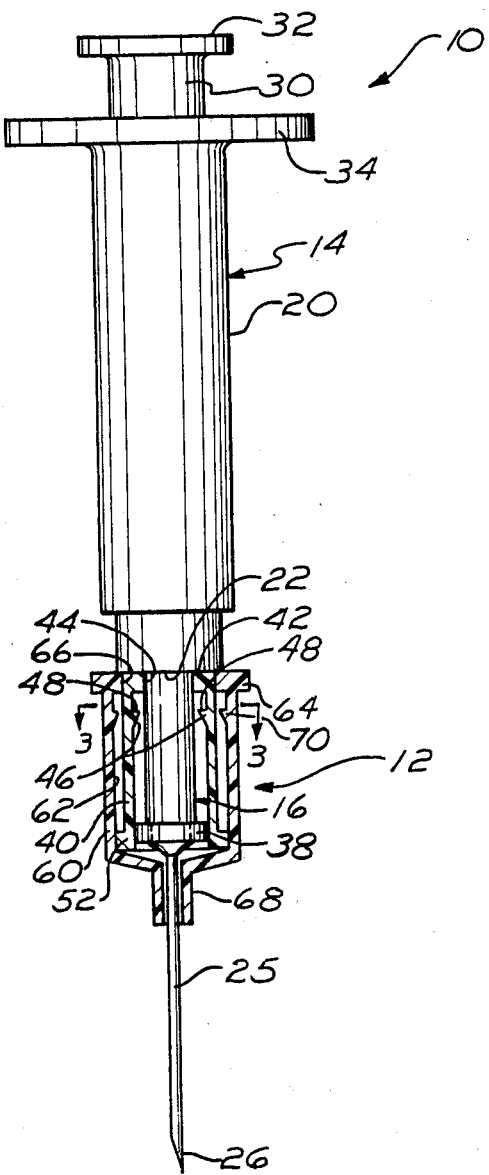
FIG. 2 is a side elevational view of a hypodermic syringe and a sectional view of a protective sheath in accordance with the present invention illustrated in a retracted mode wherein the syringe needle is exposed.
Figure 3:
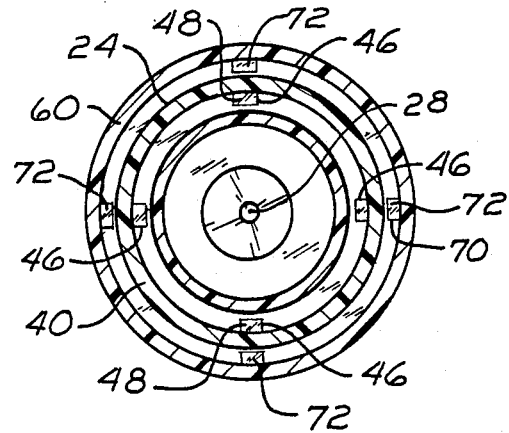
FIG. 3 is an enlarged sectional view of the syringe and protective sheath taken along the line 3—3 of FIG. 2.

It will be appreciated that the outer shield 60 is axially dimensioned to telescope over inner shield 40 and receive the inner shield in nested relationship so that the end wall portions of the respective shields are engageable against the connecting end of the main syringe body or tubing in essentially co-linear relationship as best illustrated in FIG. 2. The frictional engagement of the edge defining portions of the shield apertures 44 and 56, the frictional engagement of the peripheral edges of the mounting flange 38 against the inner cylindrical surface of shield 40, and the frictional engagement of the outer peripheral portions of the lock ring 52 against the inner cylindrical surface of shield 60 act to maintain the telescoping shield assembly in the retracted position of FIG. 2.

After usage of the hypodermic syringe or tubing, the protective needle sheath may be efficiently extended to the protective mode enclosing the needle point and permanently locked in position by axially sliding the outer shield 60 toward the needle point so as to engageably capture the inner shield 40 and continuously axially sliding the inner shield so as to engageably capture the mounting flange 38 of the hypodermic needle mounting base. The upper end wall 64 forms an exterior transverse shoulder to facilitate manual displacement of the shields to the locked extended position of FIG. 1. In practice, shield 60 is axially moved in a multi-stage telescopic fashion wherein the outer shield is axially displaced toward the needle point until the detents 70 lock against lock ring 52 of the inner shield. Continuing axial displacement of shield 60 also displaces inner shield 40 and results in detents 46 locking against flange 38.

The protective sheath may also comprise more than two telescoping shields which cooperate in an axial retracted position permit exposure of the needle point and in the extended position lock to protectively enclose the needle point.

It will be appreciated that because the protective sheath essentially mounts to the integrally extending mounting base of the needle, even in the event that the needle 16 is dismounted or disconnected from the main body portion 14 of the syringe as illustrated in FIG. 4, the protective sheath will be maintained in its protective extended position obstructing contact with the sharpened end of the needle. It will likewise be appreciated that the illustrated protective telescoping sheath is highly resistant to movement to the retracted position once the locked extended position is obtained. Consequently, the protective mode is essentially permanently maintained after usage of the syringe. Thus, the protective sheath also prevents intentional use of the needle after initial use.

With reference to FIG. 6, an intravenous catheter needle unit 80 includes an integral lock flange 82 which radially projects from a cylindrical attachment base portion 84 for the cannula 86. A one-piece protective sheath 90 of molded form includes a cylindrical shield section 92 of enlarged diameter and a distal tubular, sleeve-like shield section 94 of reduced diameter. The reduced shield section 94 slidably engages the cannula 86. The enlarged shield section 92 includes inwardly projecting detents 96 which ride over the lock flange 82 for engagement therewith to non-releasably lock the sheath in the extended protective position in a fashion as previously described for sheath assembly 12. When the protective sheath 90 is axially moved from the retracted toward the extended positions, the reduced sleeve shield section 94 slides along the cannula until shield section 94 protectively encloses the sharpened needle point 88 in the extended position.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed:

1. A hypodermic syringe assembly comprising:
   hypodermic needle means comprising a base and a connecting needle terminating in a sharpened point axially spaced from said base and forming an axial passage therethrough, said base having an axially extending portion and a retainer means transversely extending therefrom;
   syringe body means for forming a container in fluid communication with said passage and comprising mounting means for mounting said base;
   protective shield means mounted to said base for protectively shielding said needle point in an extended axial position and axially displaced from said needle point in a retracted axial position to permit exposure of said needle point, said shield means comprising first and second telescopic concentric shields generally coaxial with said needle;

said first shield having a transversely extending lock ring and defining a generally cylindrical surface slidably engageable against said retainer means and a first locking means engageable with said retainer means to lock said first shield in an extended axial position wherein said shield encloses a portion of said needle; and said second shield defining a generally cylindrical surface slidably engageable against said lock ring and comprising a second locking means engageable with said lock ring for locking said second shield in a fixed extended axial position wherein said second shield encloses said sharpened needle point.

2. The hypodermic syringe assembly of claim 1 wherein said retainer means is a generally annular flange circumferentially extending from said base in generally symmetric coaxial relationship therewith.

3. The hypodermic syringe assembly of claim 1 wherein said first locking means comprises a plurality of angularly spaced detents projecting inwardly from said first shield.

4. The hypodermic syringe assembly of claim 3 wherein said first shield is a sleeve-like member having an end wall defining an opening closely receiving the cylindrical portion of said base, said end cooperating with said detents to capture the retainer means at a first axial position of the first shield.

5. The hypodermic syringe assembly of claim 1 wherein said second locking means comprises a plurality of angularly spaced detents projecting inwardly from said second shield and engageable with said lock ring.

6. The hypodermic syringe assembly of claim 1 wherein said second shield at a distal end thereof comprises an axially extending tubular guide sleeve having a smaller diameter than the diameter of the second shield cylindrical surface, said guide sleeve enclosing the sharpened needle point in the extended position and being slidable along said needle between the retracted and extended positions.

7. The hypodermic syringe assembly of claim 1 wherein said second shield includes an end wall defining an opening, opening defining portions of said end wall closely slidably engageable against said first shield.

8. The hypodermic syringe assembly of claim 1 wherein in the retracted position, said second shield encloses said first shield in nest-like fashion, said shields having respective end walls which are generally alignable at a fixed axial position.

9. The hypodermic syringe assembly of claim 6 further comprising a flap extending interiorly of said guide sleeve, said flap being slidable along said needle and obstructing axial access to the sharpened needle point in the extended position.

10. A hypodermic needle assembly comprising:

hypodermic needle means comprising a mounting base and a needle connecting said base and terminating in a sharpened point axially spaced from said base, said base and needle defining an axial passage therethrough, said base comprising an axially extending exterior surface and having a retainer means;

protective shield means mounted to said base and resistantly axially slidable along said exterior surface between retracted and extended positions for protectively shielding said needle point in said extended position and being axially displaced from said needle point in said retracted position to permit exposure of said needle point, said shield means comprising at least first and second telescopic concentric shields generally coaxial with said needle;

said first shield comprising an integral transversely extending lock member and an interiorly disposed first locking means engageable with said retainer means to lock said first shield in an extended axial position wherein said shield encloses a portion of said needle; and said second shield comprising an interiorly disposed second locking means for locking said second shield in a fixed extended axial position wherein said second shield encloses said sharpened needle point.

11. The hypodermic needle assembly of claim 10 wherein said retainer means comprises a generally annular flange circumferentially extending from said base in generally symmetric coaxial relationship therewith.

12. The hypodermic needle assembly of claim 10 wherein said first locking means comprises a plurality of angularly spaced detents projecting inwardly from said first shield, said first shield being deformable to permit locking engagement between said retainer means and said first locking means.

13. The hypodermic needle assembly of claim 12 wherein said first shield is a sleeve-like member having an end wall defining an opening closely receiving the cylindrical surface of said base, said end wall cooperating with said detents to capture the first sleeve at a fixed axial position of the base.

14. The hypodermic needle assembly of claim 10 wherein said second locking means comprises a plurality of angularly spaced detents projecting inwardly from said second shield and engageable with said lock member, said second shield being deformable to permit locking engagement between said lock member and said second locking means.

15. The hypodermic needle assembly of claim 10 wherein said second shield at a distal end thereof comprises an axially extending tubular guide sleeve and a flap extending interiorly of said guide sleeve, said flap being slidable along said needle and obstructing axial access to the sharpened needle point in the extended position.

16. A hypodermic needle assembly comprising:

hypodermic needle means comprising a mounting base and a needle connecting said base and terminating in a sharpened point axially spaced from said base, said base and needle defining an axial passage therethrough, said base having a retainer means comprising a radially projecting locking member connecting therewith;

protective shield means mounted to said base and axially displaceable from a retracted to a non-retractable extended axial position for protectively shielding said needle point in said extended position, said shield means being axially displaced from said needle point in said retracted position to permit exposure of said needle point, said shield means comprising first and second shield sections;

said first shield section forming an enclosure having an interiorly disposed locking means engageable with said retainer means to lock said first shield section in said extended axial position, said locking means comprising means defining a recess for closely receiving said locking member; and said second shield section forming an enclosure comprising a guide sleeve having a diameter less than said first shield section and being axially slidable along said needle wherein said sleeve encloses said sharpened needle point in said fixed extended axial position.

17. The hypodermic needle assembly of claim 16 wherein said locking member comprises a generally annular flange circumferentially extending from said base in generally symmetric coaxial relationship therewith.

18. The hypodermic needle assembly of claim 16 wherein said first and second shield sections have generally cylindrical portions coaxial with said needle.

19. The hypodermic needle assembly of claim 16 wherein said protective shield means is at least partially maintained in the retracted position by the frictional engagement of the first shield against said base.

20. The hypodermic needle assembly of claim 16 further comprising a flap extending interiorly of said guide sleeve, said flap being slidable along said needle and obstructing axial access to the sharpened needle point in the extended position.

* * * * *